United States Patent
Berlinger et al.

(10) Patent No.: US 10,776,959 B2
(45) Date of Patent: Sep. 15, 2020

(54) DETERMINATION OF DYNAMIC DRRS

(71) Applicant: Brainlab AG, Munich (DE)

(72) Inventors: Kajetan Berlinger, Munich (DE); Birte Domnik, Munich (DE); Elisa Garcia Corsico, Munich (DE); Pascal Bertram, Munich (DE)

(73) Assignee: BRAINLAB AG, Munich (DE)

( * ) Notice: Subject to any disclaimer, the term of this patent is extended or adjusted under 35 U.S.C. 154(b) by 145 days.

(21) Appl. No.: 16/075,431

(22) PCT Filed: Feb. 16, 2016

(86) PCT No.: PCT/EP2016/053291
§ 371 (c)(1),
(2) Date: Aug. 3, 2018

(87) PCT Pub. No.: WO2017/140352
PCT Pub. Date: Aug. 24, 2017

(65) Prior Publication Data
US 2019/0043224 A1   Feb. 7, 2019

(51) Int. Cl.
*G06T 7/38* (2017.01)
*G06T 11/00* (2006.01)
(Continued)

(52) U.S. Cl.
CPC ............ *G06T 11/003* (2013.01); *A61B 6/032* (2013.01); *A61B 6/12* (2013.01); *A61B 6/486* (2013.01);
(Continued)

(58) Field of Classification Search
CPC combination set(s) only.
See application file for complete search history.

(56) References Cited

U.S. PATENT DOCUMENTS 7,327,865 B2   2/2008   Fu et al.
7,570,738 B2 *  8/2009   Khamene ............... A61B 6/032
                                                378/20
(Continued)

FOREIGN PATENT DOCUMENTS

WO   WO2015127970 A1   9/2015

OTHER PUBLICATIONS

International Search Report and Written Opinion issued in Application No. PCT/EP2016/053291 dated May 27, 2016.
(Continued)

*Primary Examiner* — Cindy Trandai
(74) *Attorney, Agent, or Firm* — Middleton Reutlinger

(57) ABSTRACT

A computer implemented method for determining a two dimensional DRR referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, the computer implemented method comprising the following steps: acquiring the 4D-CT; acquiring a planning CT, the planning CT being a three dimensional image used for planning of a treatment of the patient, the planning CT being acquired based on at least one of the sequence CTs or independently from the 4D-CT, acquiring a three dimensional image, referred to as undynamic CT, from the 4D-CT, the undynamic CT comprising at least one first image element representing the at least one primary anatomical element and second image elements representing the secondary anatomical elements; acquiring at least one trajectory, referred to as primary trajectory, based on the 4D-CT, the at least one primary trajectory
(Continued)

describing a path of the at least one first image element as a function of time; acquiring trajectories of the second image elements, referred to as secondary trajectories, based on the 4D-CT; for the image elements of the undynamic CT, determining trajectory similarity values based on the at least one primary trajectory and the secondary trajectories, the trajectory similarity values respectively describing a measure of similarity between a respective one of the secondary trajectories and the at least one primary trajectory; determining the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

12 Claims, 9 Drawing Sheets

(51) Int. Cl.
    *A61N 5/10*         (2006.01)
    *A61B 6/00*         (2006.01)
    *A61B 6/12*         (2006.01)
    *A61B 6/03*         (2006.01)
    *G16H 50/50*       (2018.01)
    *G06T 7/20*         (2017.01)
    *G06T 7/00*         (2017.01)

(52) U.S. Cl.
CPC .......... *A61B 6/5223* (2013.01); *A61B 6/5288* (2013.01); *A61N 5/1037* (2013.01); *A61N 5/1049* (2013.01); *G06T 7/0012* (2013.01); *G06T 7/20* (2013.01); *G06T 11/008* (2013.01); *G16H 50/50* (2018.01); *A61N 2005/1062* (2013.01); *G06T 2207/10076* (2013.01); *G06T 2207/10081* (2013.01); *G06T 2207/10124* (2013.01); *G06T 2207/30241* (2013.01); *G06T 2211/412* (2013.01)

(56) References Cited

U.S. PATENT DOCUMENTS

| | | | |
|---|---|---|---|
| 8,597,211 B2 | 12/2013 | Berlinger | |
| 9,014,424 B2 | 4/2015 | Berlinger et al. | |
| 9,730,654 B2* | 8/2017 | Erbel | A61B 6/025 |
| 2005/0180544 A1* | 8/2005 | Sauer | A61N 5/1049 |
| | | | 378/195 |
| 2006/0002630 A1* | 1/2006 | Fu | G06K 9/32 |
| | | | 382/294 |
| 2006/0074292 A1 | 4/2006 | Thomson et al. | |
| 2008/0037843 A1 | 2/2008 | Fu et al. | |
| 2008/0039713 A1* | 2/2008 | Thomson | A61N 5/1039 |
| | | | 600/411 |
| 2009/0279761 A1* | 11/2009 | Fei | A61B 6/12 |
| | | | 382/130 |
| 2010/0160836 A1* | 6/2010 | Berlinger | G06T 7/248 |
| | | | 600/595 |
| 2012/0106704 A1* | 5/2012 | Maurer, Jr. | A61N 5/1067 |
| | | | 378/65 |
| 2012/0109608 A1* | 5/2012 | Core | A61B 6/5264 |
| | | | 703/6 |
| 2012/0289826 A1* | 11/2012 | Graumann | A61B 6/032 |
| | | | 600/425 |
| 2017/0124708 A1* | 5/2017 | Baumgart | G06T 7/38 |
| 2017/0216627 A1* | 8/2017 | Brooks | A61N 5/1048 |
| 2018/0056091 A1* | 3/2018 | Jordan | A61N 5/1081 |
| 2018/0197303 A1* | 7/2018 | Jordan | A61B 6/4258 |
| 2019/0223278 A1* | 7/2019 | Jordan | A61B 6/463 |

OTHER PUBLICATIONS

Gendrin, et al. "Monitoring tumor motion by real time 2D/3D registration during radiotherapy" Radiotherapy and Oncology. vol. 102. Feb. 15, 2011.

* cited by examiner

DETERMINATION OF DYNAMIC DRRS

TECHNICAL FIELD

The present invention relates to the technical field of processing x-ray images of patients, in particular three-dimensional x-ray images, in particular so-called x-ray computed tomography (x-ray CT, in the following short "CT"), also referred to as CT scan.

In more detail, the present invention relates to the digital reconstructing (also called "rendering") of three-dimensional x-ray images (CTs) into two-dimensional images. Those two-dimensional images are referred to as in the art as DRRs. The DRR represents a simulated two-dimensional x-ray under the precondition of a particular (assumed) imaging geometry. The definition of imaging geometry is given below. For example, the rendering is performed so that the particular imaging geometry corresponds to the imaging geometry of at least one (for example one or two) monitoring x-ray device (for generating two dimensional x-ray images) which is used for monitoring a position of a patient in order to place a patient for radiotherapy or radiosurgery in accordance with a plan (for example based on a planning CT). For example an isocenter of the radiotherapy or radiosurgery device and/or an isocenter of the planning CT and/or an isocenter of the particular imaging geometry and/or and isocenter of the at least one monitoring x-ray device are identical.

For example, in the medical field of radiotherapy or radiosurgery (in the following, and in an unlimiting manner the term "radiotherapy" is used only, but has to be understood to cover at least one of radiotherapy or radiosurgery), CTs are used for planning a radiotherapeutic treatment of a patient (for example to treat the targets, for example tumors). The CTs used for planning a radiotherapeutic treatment are referred to in the art as "planning CTs". Planning CTs are used to position the patient during the radiotherapeutic treatment. The radiotherapeutic treatment uses ionizing radiation (particles and/or electromagnetic waves) which are energetic enough to detach electrons from atoms or molecules inside the body and so ionize them. The treatment radiation is for example used in radiotherapy, for example in the field of oncology. For the treatment of cancer in particular, the parts of the body comprising a tumor (which is an example for a "treatment body part") are treated using the ionizing radiation. Since the body and in particular the treatment body part can be moved during positioning of the patient for radiation treatment or during the radiation treatment, it is advantageous to control the position of the treatment beam such that the treatment beam hits the treatment body parts as accurately as possible.

The movements of the treatment body parts are in particular due to movements which are referred to in the following as "vital movements". Reference is made in this respect to the European patent applications EP 0 816 422 and EP 09 161 530 as well as EP 10 707 504 which discuss these vital movements in detail.

In order to determine the position of the treatment body part, analytical devices such as x-ray devices, CT devices, and CBCT devices are used to generate analytical images of the body. The analytical devices are in particular devices for analyzing a body of a patient, for instance by using waves and/or radiation and/or beams of energy in particular electromagnetic waves and/or radiation and/or ultrasound waves and/or particle beams. The analytical devices are in particular devices which generate the above-mentioned two or three-dimensional images of the body of the patient (in particular of anatomical body parts) by analyzing the body.

However, it can be difficult to identify the treatment body part within the analytical image (for instance two-dimensional x-ray image). To this end, the above-mentioned DRRs which are generated from a planning CT in a usual manner are used by an operator to identify the treatment body part in a two-dimensional x-ray image. To this end for instance the (usual) DRR is overlaid over an x-ray image generated when the patient is placed for treatment by means of the ionizing radiation or the DRR is placed aside the two dimensional x-ray image on a display.

SUMMARY

The methods, programs, program storage media, computers and systems as defined by the appended claims represent aspects of the invention. Advantages, advantageous features, advantageous exemplary embodiments of the aspects are disclosed in the following and in the subject-matter of the dependent and independent claims. Different advantageous features can be combined in accordance with the invention wherever technically expedient and feasible. Specifically, a feature of one exemplary embodiment or example which has the same or a similar function to another feature of another exemplary embodiment or example can be exchanged with said other feature, and a feature of one exemplary embodiment or example which adds an additional function to another exemplary embodiment can in particular be added to said exemplary embodiment.

Definitions

The method in accordance with the invention is for example a computer implemented method. For example, all the steps or merely some of the steps (i.e. less than the total number of steps) of the method in accordance with the invention can be executed by a computer (for example, at least one computer). An exemplary embodiment of the computer implemented method is a use of the computer for performing a data processing method. An exemplary embodiment of the computer implemented method is a method concerning the operation of the computer such that the computer is operated to perform one, more or all steps of the method. For example, one or more steps of the method can be performed in sequence. For example one or more steps of the method can be perform simultaneously as long as a step has not necessarily to be performed before another step. Mentioning a list of steps herein does not fixedly define a sequence, as long as a step mentioned before another step is not necessary to perform the other step.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific exemplary embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable, for example computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the exemplary embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The movements of the treatment body parts are for example due to movements which are referred to in the following as "vital movements". Vital movements can be cyclic movements which can for example be caused by breathing which is performed in accordance with a breathing cycle. Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. Analytical devices for example use imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_v-mat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity of images is preferably measured by way of a measure of similarity for images (also referred to in the following as a "image similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or image similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine an image similarity measure.

An image similarity measure can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of applying ionizing radiation to a patient for therapy (e.g. radiotherapy or radiosurgery).

A 4D-CT is a sequence of three-dimensional CTs. The 4D-CT for example allows to take moving pictures with x-rays. According to an exemplary embodiment, the moving pictures are sorted into "bins", each bin representing one CT which is assigned to a particular point in time. According to exemplary embodiment, for each breathing cycle (which cycles between exhalation and inhalation) several "bins" (CTs) are generated. The sequence of CTs is referred to herein as 4D-CT.

The 4D-CT of a body can show different kinds of movement by the body parts represented in the analytical images of the sequence. The body parts represented by the analytical images are subject to vital movements (see for instance EP 08 169 422.6 and EP 09 160 153.4 as mentioned above). This means that the body parts are moved due to vital functions of the body such as respiration and/or the beat of the heart. Respiration has usually the dominating influence on the vital movements. Different body parts undergo different changes in position depending on the cause of the vital movement. The magnitude, direction, velocity, acceleration and/or frequency of a change in position can for example differ in accordance with the cause for the change in position and/or in accordance with the position or type of the body part which undergoes the change in position. Body parts moved by the beat of the heart, for example, generally show a smaller amplitude in their changes in position than body parts which are moved due to respiration. In particular, the direction of changes in position, in particular the direction of movements, can differ depending on the cause, i.e. for example, the direction of a movement by a body part caused by respiration differs from the direction of a movement by a body part caused by the beat of the heart. The frequency of changes in position is also for example higher if they are caused by the beat of the heart than if they are caused by respiration.

If, for example, bone structures such as ribs and a diaphragm are shown in an analytical image (CT), these body parts can undergo different changes in position, in particular in different directions, even if due to the same cause such as for instance respiration. The differences between the changes in position are then in particular due to the different types of body parts and/or due to the different positions of the body parts. It is possible for the treatment body part (for example, the tumour) to undergo changes in position which differ from both the changes in the position of the diaphragm and the changes in the position of the bone structure (ribs).

End of Definitions

According to exemplary embodiments described herein, there is at least one "primary anatomical element". This at least one primary anatomical element corresponds for example to a treatment body part (e.g. tumor) or to one or more other anatomical elements (for example secondary anatomic elements). For example the one or more other anatomical elements are anatomic elements which undergo a vital movement. For example, the other anatomical element is the heart, diaphragm, or rip cage or part thereof. For example, the at least one primary anatomic element is an anatomic element which is represented by at least one voxel (for example cluster of voxels) in for example the undynamic CT or planning CT. The at least one primary anatomical element undergoes particular vital movements. The primary anatomical element can be identified by an operator (for example physician or physicist) in a undynamic CT or in a planning CT. Other anatomical elements, in particular the reminder of anatomical elements shown in the undynamic CT or the planning CT are referred to herein as secondary anatomic elements. Those secondary anatomical elements can or cannot undergo vital movements or can or cannot undergo the same vital movements as the primary anatomical elements. According to at least one exemplary embodiment, an anatomical atlas is used for segmentation of the undynamic CT or the planning CT to identify at least one of primary and secondary anatomical elements. According to at least one exemplary embodiment, an anatomical atlas is used for segmentation of the undynamic CT or the planning CT to segments unlikely to undergo vital movements and to exclude those segments from a determination of trajectories (see below) in order to save processing time and/or to make the determination of the dynamic DRR more robust. For example a vertebral column could be identified to be not subjected to vital movements and corresponding image elements of the 4D-CT could be excluded from the determination of the trajectory similarity values as described below.

According to an exemplary embodiment, the primary anatomical element is represented by at least one voxel, usually a cluster of voxels in the planning CT. The term "a primary anatomical element" does not exclude that there is more than one anatomical element but covers the expression "at least one primary anatomical element". If there is more than one primary anatomical element than those undergo the same vital movements according to an exemplary embodiment. If there is more than one primary anatomical element those are for example distinct, i.e. separated by secondary anatomical elements. According to an exemplary embodiment, there are more than one primary anatomical element and for example the more than one primary anatomical elements are represented by a plurality of imaging elements in the planning CT or 4D-CT. For example, at least some of which are adjacent. For example at least some of which are distinct.

Acquisition of Basic Data

According to at least one exemplary embodiment, 4D-CT data (short "4D-CT") are acquired. The 4D-CT represents a sequence of three-dimensional medical computer tomographic images (sequence of CTs) of an anatomical body part of a patient. The respective three-dimensional images (CTs) of the sequence for example represent the anatomical body part at different points in time. For example, the anatomical body part adopts different positions during a vital movement (e.g. caused by breathing and/or heartbeat). For instance, each CT (also referred to as "volume" or "bin" in the art) corresponds to a specific respiratory state which can be described as percentages of the fully inhaled or fully exhaled state of the patient.

For example, a plurality of different respiratory states are described by the sequence, for example, at least three, for example at least five different respiratory states are respectively described by at least one CT (bin).

For example, the extremes of the cyclic movement (for instance maximum inhalation and/or maximum exhalation) are respectively described by one CT of the sequence.

As mentioned above, one advantage of the exemplary embodiments described herein is that additional information can be provided (for example to an operator) which allows for a better interpretation and/or analysis of the CT and/or the two dimensional x-rays generated for monitoring the position of the patient. According to at least one exemplary embodiment, one of the CTs (bins) of the sequence or a CT determined by interpolation between two CTs defines the planning CT. For example, the interpolation represents a state of the body part intermediate between two neighboring states (respectively described by a sequence CT) which are subsequently adopted by the body part which undergoes the vital movement (for example cyclic movement).

For example, if the 4D-CT does not define the planning CT (e.g. in that one of the CT of the sequence is the planning CT or in that an interpolation of at least two of the CTs of the sequence defines the planning CT), then the planning CT is acquired separately.

Determination of Trajectory Similarity Values

In the following, the determination of trajectory similarity values is described. This determination based on the 4D-CT represents in itself a separate exemplary embodiment which can be supplemented by other steps of other exemplary embodiments (for example a step of displaying the trajectory similarity values) or the determination of the trajectory similarity values of image elements is embedded in at least one exemplary embodiment as described herein.

According to at least one exemplary embodiment a three-dimensional image is acquired from the 4D-CT. The acquisition of the image can for instance be done by selecting one of the CTs (bins) of the sequence defined by the 4D-CT or by determining a three-dimensional image by means of interpolation (as described above) from the 4D-CT. Thes three dimensional image is referred undynamic CT and for example comprises at least one first image element representing the primary anatomical element. For instance, a plurality of voxels of the undynamic CTs (for instance a cluster of voxels) represents the primary anatomical element (for instance target). For example, only one voxel represents a particular one of the at least one primary anatomical element, for example only one primary anatomical element. The second image elements represent the secondary anatomical elements. For example the undynamic CT is selected by an operator from the sequence CTs to be that one in which a tumor is best discernable. An example for determining a CT suitable for tumor identification and for positioning the patient is given in the following application: WO 2015/127970. According to at least one exemplary embodiment, the undynamic CT is used to determine trajectories. A trajectory which describes the path of a first image element and is referred to as "primary trajectory". A primary trajectory describes the path of the first image element as a function of time. For example, the trajectory describes the path defined by positions of the first image element for different points in time which the first image element adopts in different sequence CTs. The different points in time correspond to different states of the cyclic movement (vital movement) of the primary anatomical element (for instance target). For example the primary trajectory describes in a representative manner the trajectory of more than one first image element as described below.

According to an exemplary embodiment, one of the first image elements in the undynamic CT is defined to correspond to the isocenter of the planning CT. For example, this first image element (which is for example one voxel or more voxels) is referred to as reference image element and used to determine a primary trajectory referred to as reference primary trajectory which describes the path of the reference image element for this one image element. The reference primary trajectory can be used for calculation of the trajectory similarity value as explained below.

According to a further exemplary embodiment, the reference image element is defined to be that one which is the center of mass of the at least one primary anatomical element (for example center of mass of tumor). Thus, the reference primary trajectory is the trajectory of the center of mass. According to a further exemplary embodiment, the center of mass and the isocenter are identical.

According to a further exemplary embodiment, the reference primary trajectory can be acquired by determining a plurality of trajectories each one describing a trajectory of one or more of the at least one first image elements. Thus a plurality of trajectories are determined which represent the movement of more than one first image element which represent the at least one primary anatomical element. Then the reference primary trajectory is determined by averaging the plurality of trajectories. The averaging can be performed by different mathematical methods, for instance by at least one of mean or mode or median or by weighing particular trajectories (for instance by weighing a trajectory which represents the center of the primary anatomical element (for instance calculated by means of "center of mass" calculation where each voxel is assumed to have the same weight) or the isocenter of the planned radiation treatment) or a combination of the aforementioned methods.

The secondary trajectories respectively describe the trajectory of at least one second image element. For example, a second trajectory may describe the trajectory of only one image element or the second trajectory may describe the trajectory of a plurality (e.g. cluster) of second image elements. The determination of the first and second image elements can in particular be performed by segmentation of the undynamic CT by using an anatomical atlas. For example, image elements are excluded from trajectory determination which are part of an anatomical segment (determined by means of an atlas) which is known to do not undergo vital movements.

According to an exemplary embodiment, the aforementioned at least one primary trajectory and the secondary trajectories are used for determining the trajectory similarity values. The trajectory similarity values respectively describe a similarity between the primary and secondary trajectories. The trajectory similarity value describes in particular a similarity in positional changes of the trajectories (for example correlation, for example correlation coefficient) and/or a similarity of amplitude of cyclic movement (for example similarity of absolute maximum and/or minimum amplitude of the cyclic movement described by the compared trajectories).

According to at least one exemplary embodiment, a respective trajectory similarity value describes a similarity between a respective one of the second trajectories and one of the at least one primary trajectories (which is for example the reference primary trajectory) and/or between a respective one of the at least one primary trajectory and one of the at least one primary trajectories (which is for example the reference primary trajectory).

The trajectory similarity value is for example calculated by using the sum of squared differences (or for example an absolute value function) for each coordinate in which the trajectories is described. The sum of square of differences (or for example absolute value function) can be weighed in dependence on the coordinate. For example, the coordinate system is an orthogonal coordinate system. For example, one or more of the axes of the coordinate system are chosen to be directed along a major movement direction of the vital movement, for example inferior-superior or anterior-posterior. For example, the axes of the coordinate system are the main axes of a three dimensional surface (for example surface of a rotational ellipsoid), the surface being spanned by at least one of the trajectories, for example the reference primary trajectory which describes a cycling movement. For example, the main axes of the rotational ellipsoid can represent the axes of the coordinate system. For example, one of the minuend and subtrahend of the squared difference describes a deviation of a position one of the (primary or secondary) trajectory adopts at a particular point in time (that is the position of an image element (for example a first or second image element)) from an average position the trajectory adopts for the particular point in time (the point in time being within the time covered by the sequence described by the 4D-CT). For example, the average position is determined for one of the coordinate axes and averaged over all points in time (of the sequence). For example, the other one of the minuend and subtrahend of the squared difference describes a position which is adopted by one of the primary trajectories, for example by the reference primary trajectory. Thus, the squared difference is a measure for deviation along an axis. Any other function being a measure for such a deviation and the result of which is independent from an algebraic sign, like the absolute value function, can be used.

The similarity values can also be calculated by using a calculation of correlation coefficients which are for example a measure of the similarity of the trajectories.

The similarity measure (described by the trajectory similarity values) describes for example a similarity of the trajectories which describes for example a similarity of the movement of the image elements described by the trajectories.

The trajectory similarity values can be normalized. The trajectory similarity values can be a function of the peak to peak amplitude. According to exemplary embodiment, the trajectory similarity value describes at least one of the following: the similarity of the movement (e.g. described by correlation coefficient or sum of square differences) or the similarity of the amplitude (for instance peak to peak amplitude) described by the trajectories or the frequency of the cyclic movements described by the trajectories. Details of examples of the calculation of the trajectory similarity value are given below in the description of the detailed exemplary embodiments. According to an exemplary embodiment, the trajectory similarity value describes at least the correlation of the paths of the trajectories and/or of the movements described by the trajectories. According to an exemplary embodiment, for each of the secondary trajectories, the trajectory similarity value is calculated which describes for each of the secondary trajectories the correlation between the secondary trajectory and at least one of the at least one primary trajectory, for example reference primary trajectory. According to an exemplary embodiment, the trajectory similarity value determined in dependence on the correlation coefficient is additional a function of the similarity of the amplitude and/or similarity of the frequency. The function comprises in particular a threshold function. According to an exemplary embodiment, image values of a particular image element of the dynamic DRR are determined as a function of the trajectory similarity values. For example image values are set to black level (lowest brightness) during rendering of the DRR if all trajectory similarity values related to the image values of all image elements used for rendering the particular image element are lower than a threshold value. According to another exemplary embodiment image values of image elements of a planning CT are disregarded (for example by setting them to black level) during rendering of the dynamic DRR if the trajectory similarity value related to the image values of the image used for rendering (for example planning CT or dynamic planning CT) is lower than a threshold value or are changed in color value, for example set to lower brightness than before or changed in color, for example set to a particular color (for example red). According to another exemplary embodiment image elements of a dynamic planning CT are set to black level if the trajectory similarity value related to them is lower than a threshold value or are changed in color value, for example set to lower brightness than before or changed in color, for example set to a particular color (for example red). According to another exemplary embodiment image values of the similarity image or the transformed similarity image are set to black level if the trajectory similarity value related to them is lower than a threshold value or are changed in color value, for example set to lower brightness than before or changed in color, for example set to a particular color (for example red). For example, image values related to trajectory similarity values above a predetermined threshold remain unchanged are not influence by the trajectory similarity values, and remain for example unchanged during determination of the dynamic DRR or their color value is changed, for example are set to higher brightness than before or changed in color (for example hue or saturation), for example set to a particular color (for example green), for example color different from that color set in case of below threshold value.

Determination of the Dynamic DRR

The trajectory similarity values determined as described above are preferably used to determine the dynamic DRR. According to at least one exemplary embodiment, the dynamic DRR is designed to reflect dynamic information on the movements (for example relative movement and/or amplitude and/or frequency) described by the at least one primary trajectories (for example reference primary trajectory) and the secondary trajectories, for example the movement relative to each other, the information being reflected in at least some of the image elements of the dynamic DRR and reflect information of movement related to image elements used for rendering the dynamic DRR. According to at least one embodiment, the dynamic DRR reflects information on the dynamics of anatomic elements in relationship to the dynamics of the at least one primary anatomic element. The information on dynamics (e.g. vital movement) is included in the dynamic DRR which is helpful for identification of the at least one primary anatomic data elements (for example helpful for more reliable target identification) in for example, the dynamic DRR and/or the dynamic CT and/or the similarity image. The information on dynamics helps for an identification of secondary anatomic elements having similar (for example same) vital movements as the at least one primary anatomic element (for example target), in addition to or alternatively to an identification of the at least one primary anatomic element. For example, those secondary anatomic elements identified in the dynamic DRR having similar (for example same) vital movement as the at least one primary anatomic elements are used for positioning a patient (for example for radio therapeutic treatment) for example relative to a beam arrangement (for example treatment beam).

If for example the least one primary anatomic element is an anatomic element other than a treatment body part, like for example the heart or diaphragm or rip cage or part thereof, the dynamic DRR and/or the dynamic CT and/or the similarity image allows to identify secondary anatomic elements having similar (for example same) movement dynamics (for example undergo the same vital movements), for example move in the same way as the heart or diaphragm or rip cage or part thereof.

According to at least one exemplary embodiment, the trajectory similarity values describe information on the dynamics, for example movements (for example relative movement and/or amplitude of (cyclic) movement and/or frequency of (cyclic) movement) described by the at least one primary trajectories (for example reference primary trajectory) and the secondary trajectories, for example information on the dynamics, for example movement (for example relative movement and/or amplitude of (cyclic) movement and/or frequency of (cyclic) movement) relative to each other, for example information on the similarity of the dynamics (for example movements) described by the at least one primary trajectories relative to the secondary trajectories.

If the 4D-CT does not define the planning CT but the planning CT is acquired independently, then preferably a transformation (referred to as "planning transformation") from the undynamic CT to the planning CT is determined and used for determining the dynamic DRR. According to at least one exemplary embodiment, at least a part of the image values of the image elements of the dynamic DRR is determined in dependence on the trajectory similarity values. The dynamic DRRs can be calculated as known in the art. That is, a particular imaging geometry can be defined. This imaging geometry is for instance defined by the position of an x-ray source and an x-ray detector. For instance, the imaginary rays of the x-ray source pass through a imaginary three-dimensional anatomical body part defined by the planning CT or the dynamic planning CT. According to at least one exemplary embodiment, the transmission properties of the image elements (for example voxels) are for example described by Hounsfield units and are for example defined by the brightness of the respective voxels. According to at least one exemplary embodiment, the trajectory similarity values assigned to the respective image elements (e.g. voxels or clusters thereof) of the three-dimensional image have an influence on the virtual absorption properties of the virtual three-dimensional anatomical body part with respect to the virtual rays passing there through. According to other exemplary embodiments, the image values of the respective image elements (e.g. voxels or clusters thereof) describing the virtual three-dimensional anatomical body part and defining the absorption properties of the respective image elements (e.g. voxels or clusters thereof) are changed in dependence on the trajectory similarity values assigned to the respective voxels before the virtual rays pass through the virtual three-dimensional anatomic body part in order to determine the dynamic DRR.

According to an aspect, the planning CT is not used for determining the dynamic DRR, and/or the similarity image and/or the dynamic CT. For example only the 4D-CT is used for determining the dynamic DRR and/or the similarity image and/or the dynamic CT, this is for example done in order to reflect the dynamics, in a static two or three images dimensional image or a sequence of those images, for example to get deeper insight in the vital movements.

According to at least one exemplary embodiment, the image values of image elements of the dynamic DRRs are determined by using (for example considering) the trajectory similarity values such that the brightness of the at least some of the image values are different compared to a DRR determined from the planning CT in a usual manner (i.e. not using the trajectory similarity values, but anything else used for the determination, for example the assumed imaging geometry is the same), such a DRR being referred to herein as "usual DRR". For example, the image values being different relate to image elements representing secondary anatomical elements. According to at least one exemplary embodiment, the image values (for instance brightness) are changed compared to the usual DRR as a function of the trajectory similarity values related to the secondary anatomical element represented by the image value. Trajectory similarity values related to primary anatomical elements are referred to herein as first trajectory similarity values. For example, the first trajectory similarity values are 1. Trajectory similarity values related to secondary anatomical elements are referred to herein as second trajectory similarity values and are for example equal to or lower than the first trajectory similarity values.

The term "related" mentioned above means for example, that they relate to the same particular anatomical element represented in at least one three-dimensional matrix which describes at least one three dimensional image. For example, a trajectory similarity value is related (for example assigned) to a particular image element (for instance voxel) of the planning CT (which particular image element has a particular position in a matrix which describes the planning CT). For example an image value of a particular image element (e.g. voxel or clusters thereof) has been modified based on the trajectory similarity value related to the particular image element, the particular image element representing a particular anatomical element.

Herein, the "positions" in a matrix mean that they relate to a particular anatomical element represented by an image element (for example voxel or cluster thereof) in a three dimensional image. "Same positions" means that they relate to the same particular anatomical element.

Instead of setting image values of image elements (voxels) representing the virtual three-dimensional anatomical body part to black level, it is also possible to disregard those image elements (voxels) when virtually passing the rays there through during rendering of the dynamic DRR. That is, those image elements are handled as if no absorption of the virtual ray happens at the location of the image element (for instance voxel). Correspondingly, if the image value (for instance brightness) is only modified and not set to for instance to minimum brightness (black level), a corresponding procedure would be to modify correspondingly the absorption of the virtual ray when passing to the corresponding image element (for instance voxel). As explained above, there are different ways to determine the dynamic DRR based on the determined trajectory similarity values. At least some of which will be explained below.

According to an exemplary embodiment, the undynamic CT is the planning CT. That is, the planning CT and the acquired undynamic CT are identical. In this case, the step of determining the dynamic DRR uses, according to an exemplary embodiment, the planning CT and the determined trajectory similarity values for determining the dynamic DRR. According to an exemplary embodiment, during determination of the DRR (for example during rendering the DRR) from the planning CT, the trajectory similarity values are considered. According to an exemplary embodiment, the "consideration of the trajectory similarity values", is performed when virtually passing the rays from the virtual radiation source through the virtual three-dimensional anatomical body part described by the planning CT. For example, the image values describe the transmission and/or absorption properties of the virtual three-dimensional body parts, for example by means of hounsfield values (for example Hounsfield units). According to an exemplary embodiment, the transmission and/or absorption properties described by the image values of the planning CT are modified in accordance with the trajectory similarity values related to (for example assigned to) the different positions of the three dimensional matrix representing the planning CT. For example, if a trajectory similarity value assigned to a particular position of the matrix indicates no similarity, then unattenuated transmission is defined for the position during rendering of the dynamic DRR.

Herein, a change, for example a modification of an image value covers at least one of change of brightness or change of color (for example change of hue and/or change of saturation).

According to a further exemplary embodiment, the brightness values of the planning CT describes the transmission and/or absorption properties of anatomical elements represented by image values of the planning CT. For example, the brightness values are modified in accordance with the trajectory similarity values assigned to the respective positions of the matrix describing the planning CT. Alternatively or additionally, the colors of the image elements are modified in accordance with the trajectory similarity values (for example red in case of low similarity and green in case of high similarity). According to this exemplary embodiment, the planning CT is modified based on the trajectory similarity values assigned to the respective image elements (e.g. voxels) of the planning CT. That is, a modified planning CT is determined based on the trajectory similarity values. This modified planning CT describes a modified virtual anatomical body part through which the virtual rays pass in order to determine the dynamic DRR. For example elements of the virtual anatomical body part are fully transmissive for x-ray, if trajectory similarity values related to these elements are below a threshold value. The planning CT modified by the trajectory similarity values respectively assigned to the image elements of the planning CT is also referred to herein as "dynamic planning CT". For example, the dynamic planning CT describes the transmission and/or absorption properties of a virtual anatomical body part through which the virtual ray pass during rendering of the dynamic DRR. Sometimes in the art, a CT generated by using contrast agents is referred to as a "dynamic CT". Herein "dynamic" is used in a different manner and a "dynamic CT" or a "dynamic planning CT" can be generated by using a contrast agent or by not using a contrast agent. Correspondingly, "undynamic" is used in a different manner and a "undynamic CT" can be generated by using a contrast agent or by not using a contrast agent.

According to further exemplary embodiments, the planning CT is not determined based on the 4D-CT but determined separately. According to an exemplary embodiment, in this case, a transformation is determined from the acquired undynamic CT to the planning CT.

Based on the trajectory similarity values determined as mentioned above, a three-dimensional image is acquired. This three-dimensional image is referred to as "similarity image". The positions of the image elements (for example voxels or clusters thereof) of the similarity image in a matrix which describes the similarity image correspond to positions of image elements of a matrix which describes the undynamic CT and the image values of the image elements of the similarity image correspond to the trajectory similarity values assigned to the corresponding image elements of the undynamic CT. For example, "corresponding positions" means that the respective trajectory similarity values are at the same positions in a matrix which describes the similarity image as the image elements of another matrix which describes the undynamic CT to which they are respectively assigned.

For example, the transformation is applied to the similarity image in order to determine a transformed similarity image. The transformed similarity image is transformed so that the image elements of the transformed similarity image are at positions in a matrix which describes the transformed similarity image which correspond to positions of image elements of another matrix which describes the planning CT, the corresponding positions relate to the same anatomical element. That is, the transformation results in that trajectory similarity values are assigned to the respective image elements of the planning CT.

For example, the dynamic DRR is determined by using the planning CT and the determined trajectory similarity values wherein, during determination of the DRR from the planning CT, the trajectory similarity values represented by the image elements of the transformed similarity image are used. That is, the attenuation of the virtual ray passing through the virtual three-dimensional body represented by the planning CT is modified in dependence on the image values of the transformed similarity image being assigned to respective image elements of the playing CT (as mentioned before). According to a further example, the image elements of the planning CT are modified based on the transformed similarity image. As mentioned above, the transformed similarity image allows to assign to each image element of the planning CT a trajectory similarity value which is a corresponding image value of the transformed similarity image. The assigned trajectory similarity value is used to change the image values of the planning CT. The term "corresponding" means in this respect that the trajectory similarity values of the transformed similarity image adopt the same position in the transformed similarity image as the corresponding image elements of the planning CT do.

The planning CT modified as mentioned above is referred to herein as "dynamic planning CT". The procedure for determining the DRR is applied to the dynamic planning CT in order to determine the dynamic DRR.

According to at least one further exemplary embodiment, the planning CT is acquired independently from the undynamic CT as described above. In this case, for example, a transformation from the undynamic CT to the planning CT is determined.

Furthermore, for example, a three-dimensional image (referred to as dynamic CT) is determined by changing image values of at least a part of the second image elements of the undynamic CT. The change of the image values is performed in dependence on the trajectory similarity values assigned to respective image elements of the undynamic CT. In other words, for the respective image elements of the undynamic CT, the respectively assigned trajectory similarity values modify the respective image value of the respective image element of the undynamic CT. For example, the trajectory similarity values are determined as mentioned above for the respective image elements of the undynamic CT and then assigned to the respective image elements of the undynamic CT for which they have been determined.

For example, the determined transformation is applied to the dynamic CT in order to determine a CT referred to as "dynamic planning CT". That is the transformation (transformations herein are spatial transformations) transforms the dynamic CT into the dynamic planning CT. At least a part of the second image elements of the dynamic planning CT reflect the previously determined correlation.

For determining the dynamic DRR, for example, the dynamic planning CT is used as a basis for digitally reconstructing the two-dimensional image from the dynamic planning CT. That is, the virtual rays pass through a virtual anatomical body part, the transmission and/or absorption properties of the elements of the body part being described by the image values of the dynamic planning CT.

According to an example of at least one exemplary embodiment, the primary and secondary trajectories are determined as described in the following. Transformations referred to as sequence transformations are determined. The sequence transformation describe transformations between sequence CTs. For example a transformation from the undynamic CT to another one of the sequence CTs (in case the undynamic CT is one of the sequence CTs). For example, the sequence transformations allow to transform between subsequent ones of the sequence CTs. For example, the sequence transformation are constituted to transform from the undynamic CT to other ones of the sequence CTs. The transformations are preferably performed by using image fusion. For example, the sequence transformations are constituted so that the positions of the image elements of a respective one of the sequence CTs can be transformed to the positions of the respective image elements in another respective one of the sequence CTs. Thus, the determined sequence transformations allow to determine a change of position of image elements in the sequence. This change of positions represents trajectories of anatomical elements described by the respective image elements.

For example, the trajectories of the at least one first image element and of at least some of the second image elements are determined by applying the determined sequence transformations to the at least one first image element and to the at least some of the second image elements.

According to at least one exemplary embodiment, the trajectory similarity values are determined based on the trajectories. According to an example of the at least one exemplary embodiment, the trajectory similarity values are determined as a function which has a positive value and is the higher the higher an absolute value of a difference between a minuend and a subtrahend is. The function is referred to as absolute difference function and is for example the function of squared differences, difference to the fourth power, sixth power . . . or a function for obtaining an absolute value of the difference. The minuend and subtrahend depend on positions of two different trajectories at a particular (same) time. One of the two trajectories being a primary trajectory, according to an embodiment the reference primary trajectory.

For example the calculation of the trajectory similarity values can be performed for each coordinate of a coordinate system in which the trajectories are at rest. For instance, a first deviation (difference) of a first image element from a mean average value of the position of the first image element can be subtracted from a second deviation (difference) of a second image element from an average position with respect to the same coordinate and then those two deviations are subtracted and for example the absolute difference function is applied to this difference.

The aforementioned positive values can be weighed differently for each coordinate axis in order to determine a value which reflects the correlation for example for all three axes of the coordination system. This determined value is for example the trajectory similarity value. Furthermore, a threshold function can be applied to value in order to obtain the trajectory similarity value.

According to at least one further exemplary embodiment, the trajectory similarity value is determined based on calculation of a correlation coefficient. For example, the trajectory similarity value is a function of a product of the aforementioned first and second deviations. For example, this function is calculated for each axis of the coordination system. The different values for different axes of the coordination system can be weighed. Optionally a threshold function can be applied to the result of the function in order to obtain trajectory similarity values.

According to a further exemplary embodiment, the trajectory similarity value is a value referred to as amplitude similarity value. For example, the trajectory similarity value is a function, for example threshold function of the amplitude similarity value. For example, the amplitude similarity value reflects similarity of amplitudes of first and second image elements while they undergo a cyclic (for instance periodic) movement. More details are given below in the detailed exemplary embodiments. The aforementioned exemplary embodiments and examples for determining the trajectory similarity value can be combined. According to a further exemplary embodiment both the correlation coefficient and the amplitude similarity value (which describes for example similarity of a peak to peak amplitude) can be combined. For example, both the correlation coefficient and the amplitude similarity value are respectively subjected to a threshold function having respective threshold values. For example, the trajectory similarity value is determined by using a function which sets the trajectory similarity value to a value which indicates similarity if both the correlation coefficient and the amplitude similarity value are above their respective threshold values. If one of them is below, then the trajectory similarity value is set to indicate "not similar" (which for example results in that a corresponding image element in the dynamic DRR is set to black level).

According to at least one exemplary embodiment of the invention, the computer implemented method further comprises the steps of determining at least one of the at least one first image element or the second image elements by using an anatomical atlas. The steps in particular comprise segmenting the undynamic CT by using the atlas. The segments achieved by means of the segmenting being identified to correspond to one or more (for instance clusters) of the second image elements and/or the at least one first image element. In particular, image elements can be excluded from the processing (for example by not calculating the trajectories for them) which are part of segments known to be not subjected to a vital movement or a vital movement which is not similar to that of the treatment body part. Or for those image elements the trajectory similarity values are set to indicate no similarity.

According to at least one further exemplary embodiment, the computer implemented method comprises the step of displaying the dynamic DRR over an x-ray image (for example by superposition) or besides an x-ray image. The x-ray image is for example used by an operator (for instance surgeon or physicist) to determine the position of a treatment body part to be subjected to treatment radiation. The display of the dynamic DRR can be used for (planning) the positioning of the patient for the radiotherapeutic treatment.

According to an example, image values (for example of the similarity image) representing the trajectory similarity values can have a brightness or color (for example hue and/or saturation) which depends on the trajectory similarity value.

According to a further aspect, a computer implemented method is provided which is for example used to determine the above mentioned similarity image and/or dynamic CT and/or dynamic DRR. The determination is for example based on a 4D-CT, for example not based on a planning CT, for example uses (only) the 4D-CT. The 4D-CT describes for example a sequence of three-dimensional medical computer tomographic images of an anatomical body part (referred to as sequence CTs). The sequence CTs represent the anatomical body part at different points in time. The anatomical body part comprises at least one primary anatomical element and secondary anatomical elements. This further aspect is for example used if no radiotherapeutic treatment is intended for the patient and if there is no need for a planning CT. This further aspect is for example used if further insights in the (anatomical) dynamics of the patient is required. With exception of the use of the planning CT, the method according the further aspect comprises one or more step combinations as described above. According to a further aspect, a complete implement method is provided which uses at least or only the steps shown in FIG. 1 for determining the trajectory similarity values. According to a further aspect, a computer implemented method is provided that uses the steps S20 and S24 of FIG. 2, while in step S24 the dynamic DRR is determined by using the undynamic CT instead of the planning CT. According to further aspects, method uses the steps in FIG. 3 with exception of step as 32. Furthermore, step 34 has changed in that the dynamic CT is determined by using the undynamic CT and the determined trajectory similarity values and by changing image values of the undynamic CT independence on the trajectory similarity values. Finally the step S36 has changed in that the dynamic DRR is determined from the dynamic CT. According to aspects, at least one of the dynamic DRR or the dynamic CT is displayed. According to a further aspect, the steps of FIG. 1 are supplemented by step of displaying the determined trajectory similarity values as three-dimensional similarity image.

The computer implemented method according to the further aspect comprises steps as mentioned below, examples for at least some of the steps are described with respect to other aspects described herein and are therefore not (again) described in detail.

For example, the 4D-CT is acquired. A planning CT is acquired. The planning CT is according to a first exemplary embodiment acquired based on the 4D-CT. For example, by interpolation between one of the sequences CTs or by defining one of the sequence CTs to be the planning CT. According to a further alternative exemplary embodiment, the planning CT is acquired independently from the 4D-CT for example by receiving CT data from a medical analytical imaging device which is constituted to generate CTs.

For example the computer implemented method further comprises the step of acquiring a three-dimensional image, referred to as undynamic CT, from the 4D-CT. For example, one of the sequence CTs is selected as the undynamic CT. The selection is for instance performed on a visual basis. For instance, an operator selects one of the sequence CTs in which a treatment body part can be visually best segmented from other body parts. According to a further example, a segmentation of the treatment body part by using an atlas has highest confidence level for the treatment body part in case of the selected sequence CT. The aforementioned features can be combined also with the other aspects mentioned before.

In a further step, for example, a trajectory is acquired, the trajectory is referred to as primary trajectory. The acquisition is for example based on the 4D-CT. The primary trajectory describes a path of the at least one first image element as a function of time.

For example, in a further step, trajectories of the second image elements are acquired. The trajectories are referred to as secondary trajectories. The acquisition is for example based on the 4D-CT.

For example, in a step trajectory similarity values are determined. The trajectory similarity values are determined for the image values of the undynamic CT. The determination is for example based on the primary trajectory and the secondary trajectories. The trajectory similarity values respectively describe a means for similarity as described herein.

For example, in another step, the similarity image is determined by determining the trajectory similarity values to be image values of image elements of a similarity image. The image elements of the similarity image are referred to as similarity image elements. The image elements of the undynamic CT are referred to as undynamic image elements. As described with respect to other aspects, the determination of the similarity image is performed so that the positions of the similarity image elements correspond to the positions of the undynamic image elements of the undynamic CT to which the trajectory similarity values are respectively related.

The acquisition of a planning CT is optional. For example, the similarity image can be determined without using the planning CT.

Optionally, in case the planning CT is not acquired based on the 4D-CT but independently from the 4D-CT, a transformation is further determined from the undynamic CT to the planning CT (examples therefore are described above with respect to the other aspect). For example the determined transformation is applied to the similarity image (examples therefore are described herein with respect to the other aspects).

According to a further exemplary step, the similarity image or the transformed similarity image is displayed For Example, the similarity image is determined for each CT of the sequence CT. For example a change of the similarity images is visualized by a movie play feature.

According to another exemplary embodiment of this aspect, the similarity image or the transformed similarity image is displayed over or besides a CT, for example sequence CT and/or planning CT. According to another exemplary embodiment, a DRR (referred to as similarity DRR) is rendered using the similarity image as the tree dimensional image in the manner described above. For example, the same imaging geometry is used for the rendering of the similarity DRR as for generation of a two-dimensional x-ray image which is for example used for placing a patient. The similarity DRR is for example display over the two-dimensional x-ray (for example superposed) or displayed besides the two-dimensional x-ray image.

According to a further aspect, a program is provided which when running on a computer or when loaded into a computer causes the computer to perform at least one of the computer implemented methods described herein.

According to a further aspect, a signal wave is provided, which carries information which represent the program according to the aforementioned aspect.

According to a further aspect, a program is provided, which comprises code means adapted to perform all the steps of at least one of the computer implemented methods described herein.

According to a further aspect of the invention, a program storage medium is provided, on which the program according to at least one of the aforementioned aspects is stored. The program is for example stored in a non-transitory manner.

According to a further aspect of the invention, a computer is provided, on which the program according to at least one of the aforementioned aspects is running or in which such a program is loaded. The computer is for example constituted to perform at least one of the aforementioned computer implemented methods. For example, the computer comprises the program storage medium of one of the aforementioned aspects.

According to further aspects of the invention, a system is provided. The system comprises for example the computer according to the aforementioned aspect. For example, the system further comprises a display device (for example a computer monitor) for displaying the dynamic DRR determined in accordance with one of the aforementioned aspects. For example, the display device is alternatively or additionally constituted to display the similarity image according to one of the aforementioned aspects. For example, the computer comprises an interface (for example a digital and/or electronic interface) for receiving data, for example the 4D-CT and/or the planning CT.

According to a further exemplary embodiment of this aspect, the system comprises a couch for placing a patient, for example for treatment with treatment radiation. The system for example further comprises according to this exemplary embodiment, a treatment device constituted to emit a treatment beam for treating the patient by means of treatment radiation.

According to a further exemplary embodiment of this aspect, the system comprises an analytical device constituted for generating the 4D-CT.

For example, according to a further exemplary embodiment, the system alternatively or additionally comprises an analytical device constituted for generating the planning CT.

DESCRIPTION OF THE FIGURES

In the following, exemplary embodiments of the invention are described with respect to the enclosed Figures in an unlimiting manner.

With respect to the Figures showing flowcharts, generally, the sequence of the steps is not obligatory but just an example. The only requirement is that data necessary for a determination step have to be acquired before the respective determination.

Figure 1:
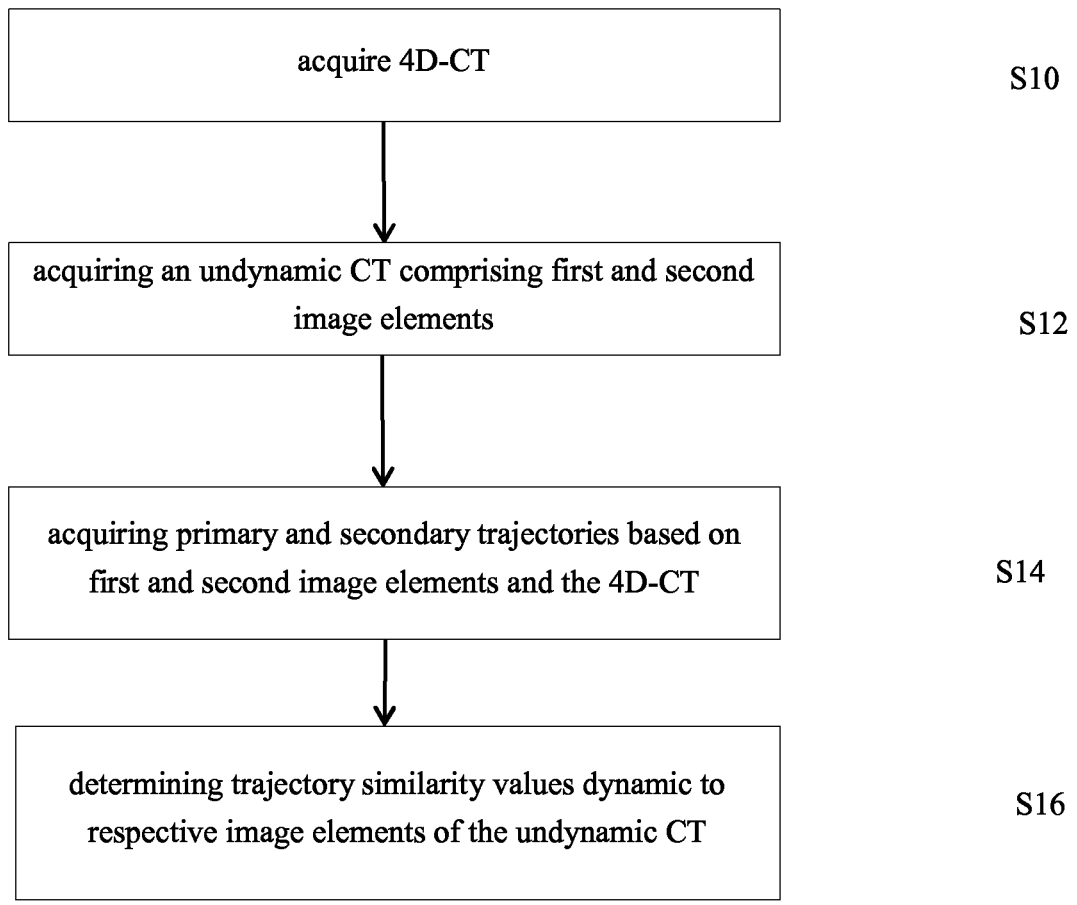
FIG. 1 shows a flowchart related to the determination of trajectory similarity values.

FIG. 1 shows steps for determining the trajectory similarity values. According to step S12, the undynamic CT is acquired. According to step S14, the primary and secondary trajectories are acquired. For example, the primary and secondary trajectories are determined based on the acquired undynamic CT, for example based on the at least one first image element and the second image elements. For example, the first image element is a tumor. For example the second image elements represent secondary anatomical elements. For example the secondary anatomical elements are discernible in an x-ray image. For example, those secondary anatomical elements have a strong interaction with x-rays (for example by absorbing the x-rays) than fluids (for example water, air).

Figure 7:
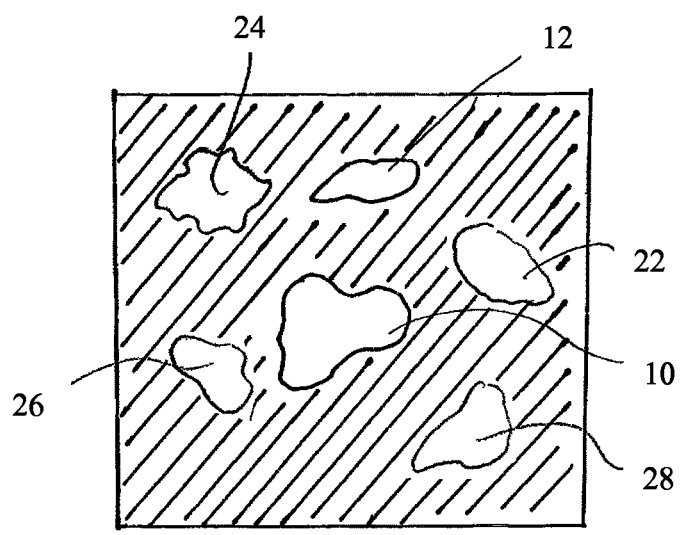
FIG. 7 shows a schematic representation of a usual DRR which was generated from a schematic planning CT in accordance with methods known in the art.

Having a reference to FIG. 7, it is assumed that FIG. 7 represents a schematic usual DRR generated from the dynamic CT which is assumed to correspond to the planning CT. Then according to an example, region 10 represents the treatment body part and is generated from a cluster of voxels of the planning CT which corresponds to the undynamic CT. That is, the region 10 in FIG. 7 corresponds to a cluster of first image elements of the undynamic CT from which the usual DRR of FIG. 7 is generated. Accordingly, according to an example, the regions 12, 22, 24, 26, and 28 are generated from clusters of second image elements of the undynamic CT (which is identical to the planning CT).

According to step S14 of the FIG. 1, primary and secondary trajectories are acquired based on first and second image elements of the undynamic CT and based on the other sequence CTs defined by the 4D-CT. As mentioned above, preferably image fusion methods are used to determine the trajectories. In a next step, for example, the trajectory similarity values related to the respective image elements of the undynamic CT are determined. For example, this is done for each voxel of the undynamic CT or for voxel clusters. According to an example, the trajectory similarity values for the voxels being inside the region generated from a voxel cluster of the undynamic CT which results in the regions 22, 24, and 26 are lower than a threshold value and the trajectory similarity values for the voxels inside the voxel clusters of the undynamic CT from which the regions 10 and 12 are generated in FIG. 7 have a value above the threshold value. Again, the aforementioned example relates to the case where the undynamic CT corresponds to the planning CT.

Detailed examples for the calculation of trajectory similarity values are given below.

Figure 2:
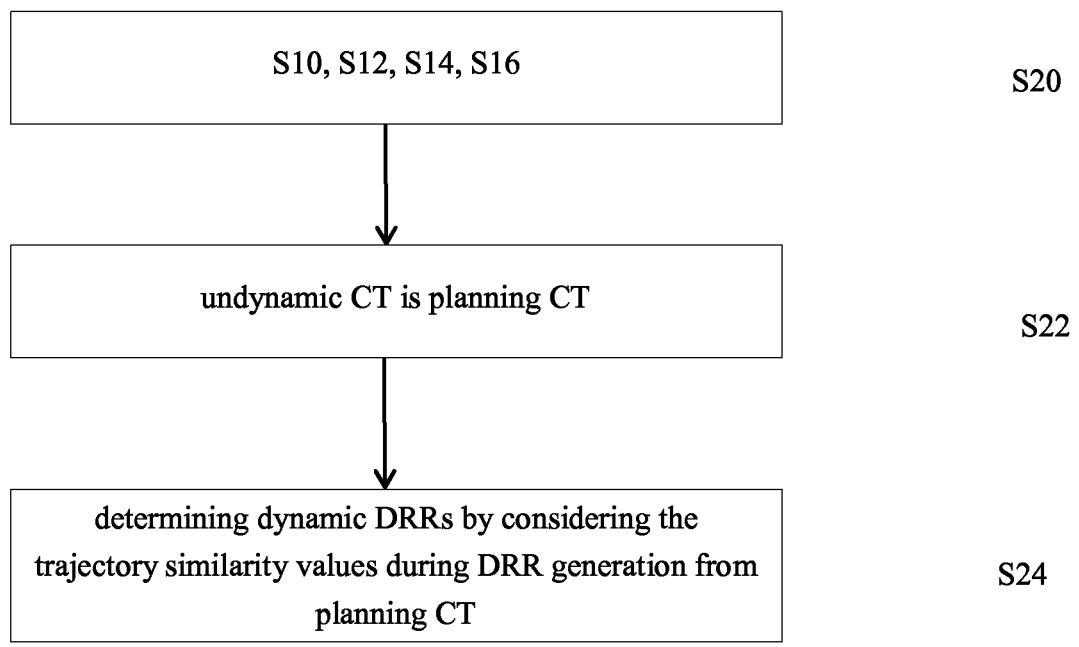
FIG. 2 shows a flowchart according to one exemplary embodiment according to at least one exemplary embodiment for determining dynamic DRRs.

FIG. 2 relates to an exemplary embodiment for determining the dynamic DRRs according to the flowchart shown in FIG. 2. According to the flowchart shown in FIG. 2, the computer implemented method relates to the case where the undynamic CT is the planning CT. For example, there is a step of selecting one of the sequence CTs as the planning CT and the undynamic CT. This step can be performed by an operator.

For example, the steps of FIG. 1 are also performed according to an exemplary embodiment described in FIG. 2. The combination of steps of FIG. 1 are indicated as step S20 in FIG. 2. For example, it can be defined that the undynamic CT should be the planning CT before or after step S20 or simultaneously to step S20 (see step S22 in FIG. 2).

Figure 8:
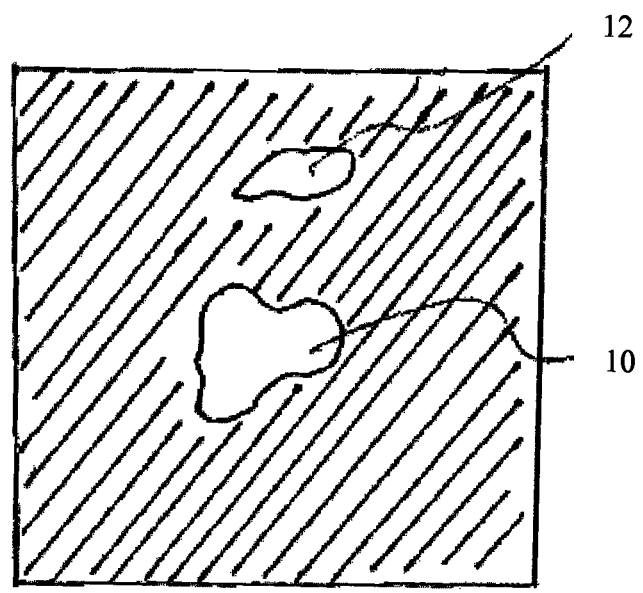
FIG. 8 shows a dynamic DRR generated from the same assumed schematic planning CT according to an example.

In step S24 the dynamic DRRs are determined by considering the trajectory similarity values during DRR generation from the planning CT. As mentioned above, the consideration can be performed by modifying the absorption properties (Hounsfield values) described by the image values of the planning CT in dependence on the trajectory similarity value assigned to the corresponding image element. For instance assume, the trajectory similarity values related to anatomical elements represented by regions 22, 24, 26, and 28 are below a threshold, then for example the image values for these regions are set to black as shown in FIG. 8.

Figure 3:
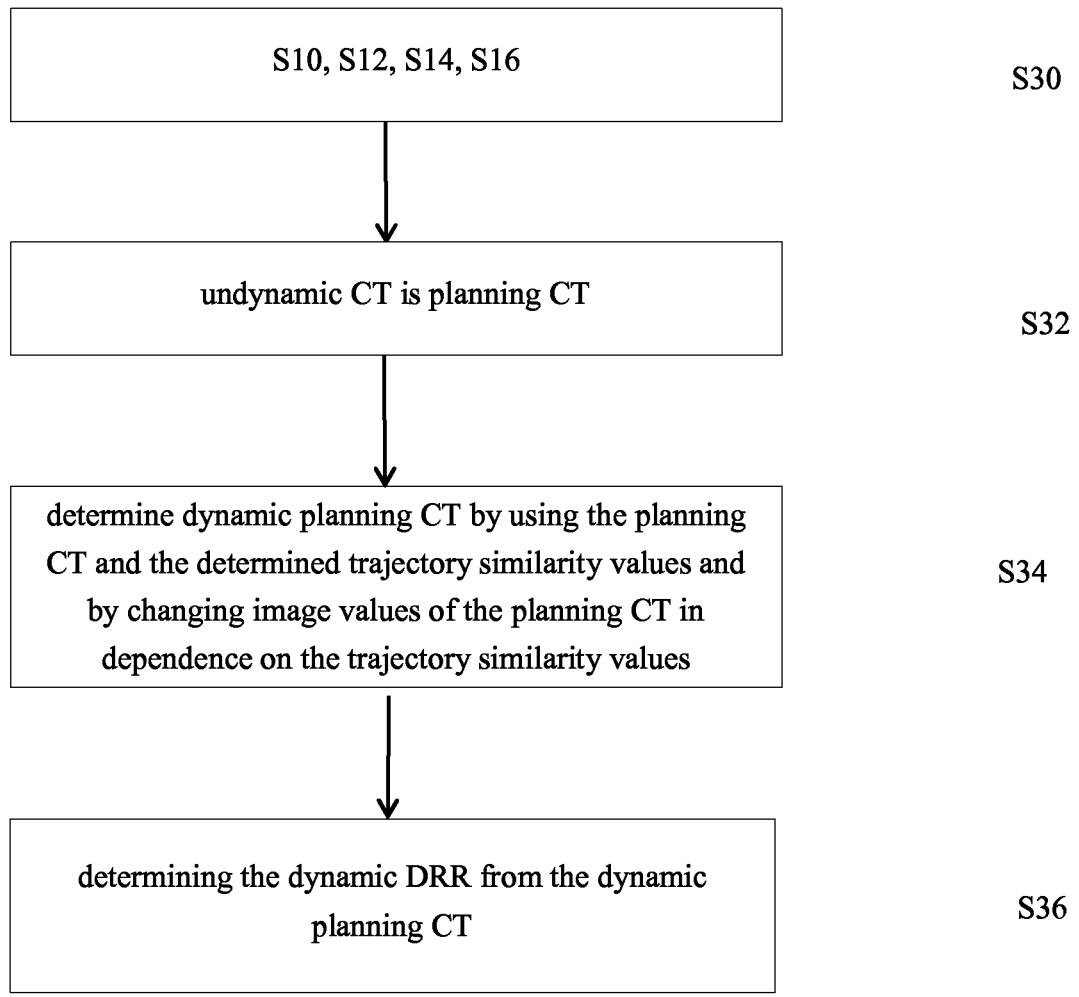
FIG. 3 shows a flowchart according to one exemplary embodiment according to at least one exemplary embodiment for determining dynamic DRRs.

FIG. 3 is a further flowchart which represents at least one further exemplary embodiment.

The steps S30 and S32 correspond to steps S20 and S22 in FIG. 2 and can be interchanged or performed simultaneously.

According to step S34, the dynamic planning CT is determined by using the planning CT and the determined trajectory similarity values and by changing the image values of the planning CT in dependence on the trajectory similarity values. For example, the image values of the planning CTs represent Hounsfield values which are a measure for the interaction of the corresponding anatomical body part represented by the image value with the x-rays. By changing the image values of the planning CT in dependence on the trajectory similarity value, the subsequent determination of the dynamic DRR is influenced. This determination is performed in step S36. The dynamic DRR is performed in the usual manner of generating a DRR but not based on a usual planning CT but on the dynamic planning CT determined in step S34.

Figure 4:
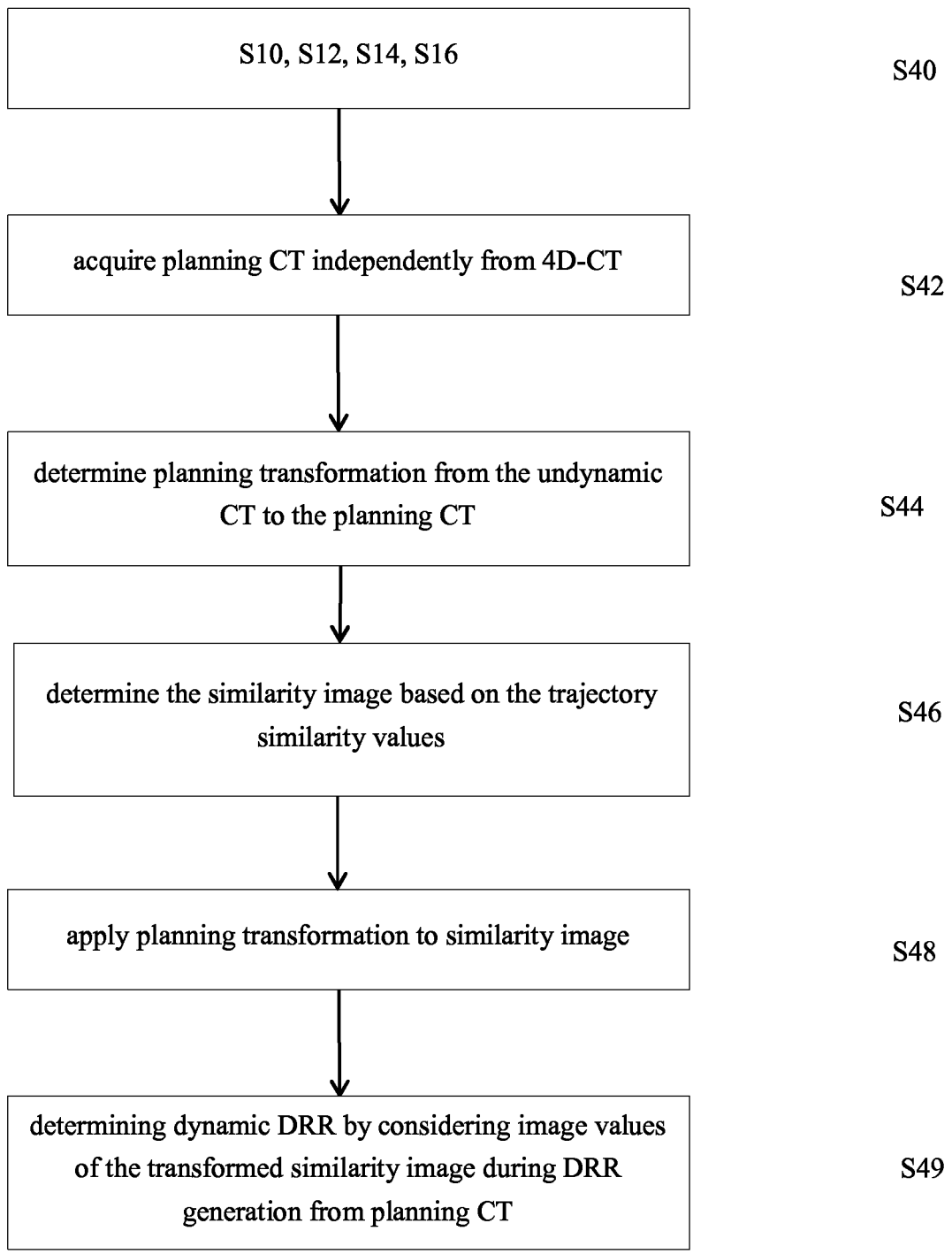
FIG. 4 shows a flowchart according to one exemplary embodiment according to at least one exemplary embodiment for determining dynamic DRRs.

According to the at least one exemplary embodiment shown in FIG. 4, there is first the step S40 which corresponds to the combination of steps shown in FIG. 1. Before, after or simultaneously this step, a step S42 is performed for acquiring a planning CT independently from the 4D-CT. This step is step S42. Based on the undynamic CT determined in step S40, a planning transformation is determined from the undynamic CT to the planning CT for instance by using image fusion. This is done in step S42.

The step S46 can be performed before S42 or step S44 or simultaneously thereto, for example. The step S46 uses the trajectory similarity values determined in step S40 to determine the similarity image explained above.

According to step S48, the planning transformation determined in step S44 is applied to the similarity image.

According to step S49, the dynamic DRR is determined by considering image values of the transformed similarity image during DRR generation from the planning CT. The "consideration of image values" is performed in the same manner as described above with respect to the generation from the planning CT in step S24.

Figure 5:
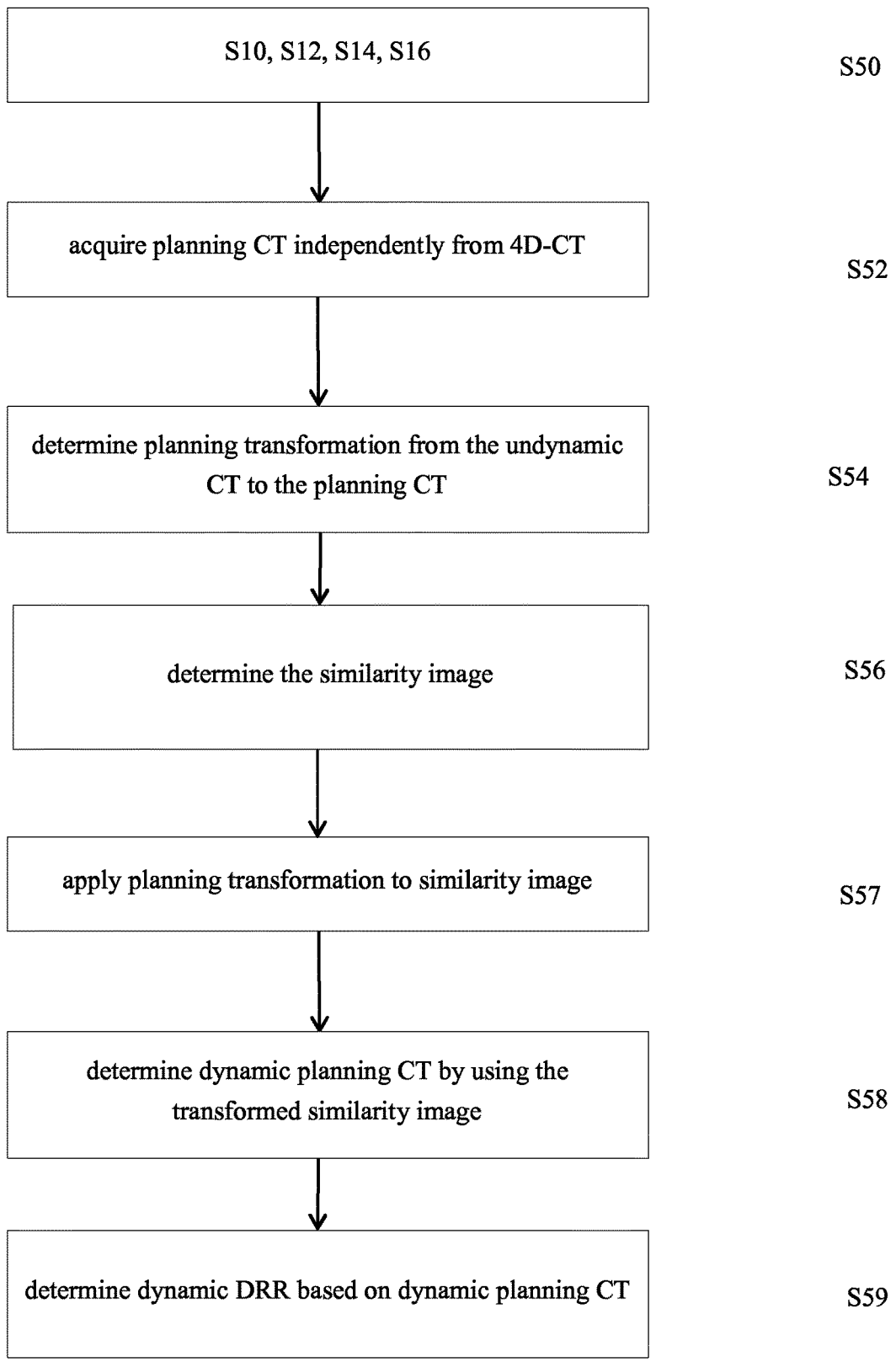
FIG. 5 shows a flowchart according to one exemplary embodiment according to at least one exemplary embodiment for determining dynamic DRRs.

According to the at least one exemplary embodiment shown in FIG. 5, which is an exemplary flowchart, a step S50 is performed, which comprises the steps of the FIG. 1.

For example, a step S52 is performed, which relates to the acquisition of the planning CT independently from the 4D-CT. That is, the patient is for instance before or after the generation of the 4D-CT subjected to medical image generation by means of an analytical device for generating a CT. According to at least one exemplary embodiment, the planning CT is static and not time dependent.

According to the step S54, a planning transformation is determined from the undynamic CT to the planning CT. For example, this is performed in the manner as described before with respect to step S44.

According to step S56, the similarity image is determined by using the trajectory similarity values determined in step S50. For example, the step S56 is performed before or after step S54 or before or after step S52 or simultaneously to one of those steps.

According to step S57, the planning transformation is applied to the similarity image for determining a transformed similarity image.

For example according to a further step S58, the dynamic planning CT is determined by using the transformed similarity image. That is, the trajectory similarity values of image elements of the similarity image are used to modify image values of corresponding image elements of the planning CT. "corresponding image elements" are image elements which are at the same position in the planning CT as corresponding image elements in the similarity image.

For example, in a step S59, the dynamic DRR is determined based on the dynamic planning CT by applying usual methods known in the art for determining a DRR from a CT.

Figure 6:
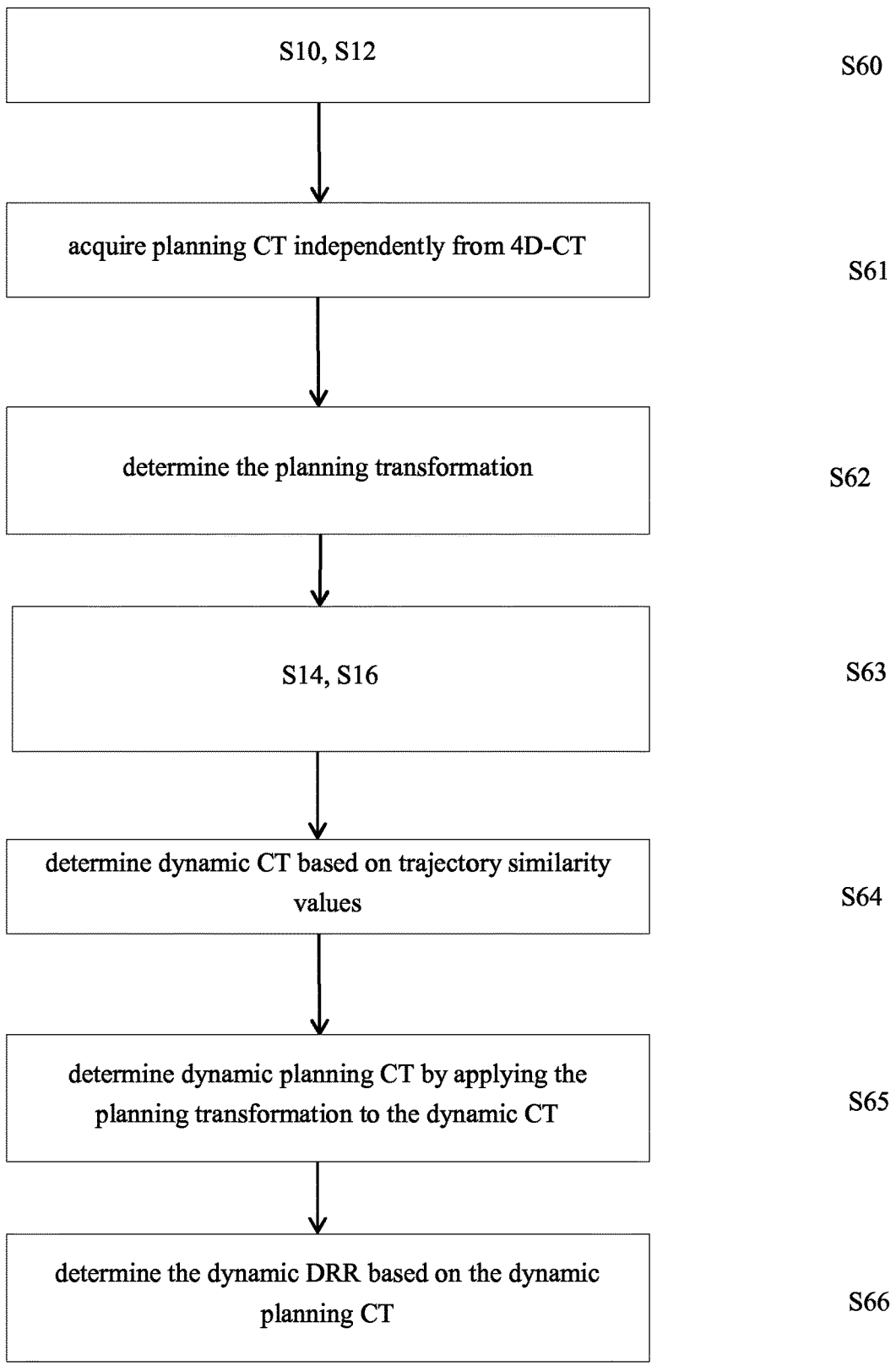
FIG. 6 shows a flowchart according to one exemplary embodiment according to at least one exemplary embodiment for determining dynamic DRRs.

According to at least one further exemplary embodiment, a flowchart shown in FIG. 6 describes method steps of the at least one further exemplary embodiment. According to step S60, the steps S10 and S12 are performed. According to step S61 the planning CT is acquired independently from a 4D-CT as described above with respect to step S42 or step S52. For example, the step S60 is performed before, after or simultaneously to step S61 or S62.

For example, according to step S62, the planning transformation is determined based on the undynamic CT and the planning CT.

For example in a step S63, the steps S14 and S16 of FIG. 1 are performed for determining the trajectory similarity values. For example, the determined trajectory similarity values are used in step S64 to determine the dynamic CT. The dynamic CT is a three-dimensional image which is for example determined by changing image values of the undynamic CT. The change is performed based on the trajectory similarity values determined in step S63. For example, in step S63 the trajectory similarity values are determined for particular image elements of the undynamic CT. That is, the trajectory similarity values are assigned to the respective image elements. The assigned trajectory similarity values are then used to change the image values of image elements of the undynamic CT in step S64. For example, this is at least done for at least a part of the second image elements. For example, this is done in case the trajectory similarity values are below a predetermined threshold.

For example, according to another step S65, the dynamic planning CT is determined by applying the planning transformation to the dynamic CT.

For example, according to a step S66, the dynamic DRR is determined based on the dynamic planning CT in a manner which is usual for determining a DRR from a CT.

FIG. 7 has already been described above.

FIG. 8 represents a schematic and exemplary example of a dynamic DRR. It is assumed that the region 10 represents the treatment body part (for instance tumor). FIG. 12 represents a region which has been generated from the planning CT. The region represents the DRR projection of a voxel cluster. The trajectory similarity values assigned to the voxel cluster are above a predetermined threshold value. That is, the region 12 represents a body part which undergoes a similar vital movement as the treatment body part 10. The term "similar" covers herein identical and the usual meaning of "similar". For example, image values related to trajectory similarity values above a predetermined threshold remain unchanged are not influence by the trajectory similarity values, and remain for example unchanged during determination of the dynamic DRR. In FIG. 8, the regions 22, 24, 26 and 28 are missing since the trajectory similarity values relating to those regions are below a predetermined threshold value. According to a exemplary alternative embodiment, the trajectory similarity value is a value which represents the result of application of the threshold function. That is, the trajectory similarity value is for example a binary value which is for example zero for "non-similarity" and one for "similarity". That is, in this exemplary embodiment, the trajectory similarity values for the voxel clusters which represent the regions 22, 24, 26 and 28 in the planning CT are related to trajectory similarity values which indicate non-similarity (for example having a value of 0).

Figure 9:
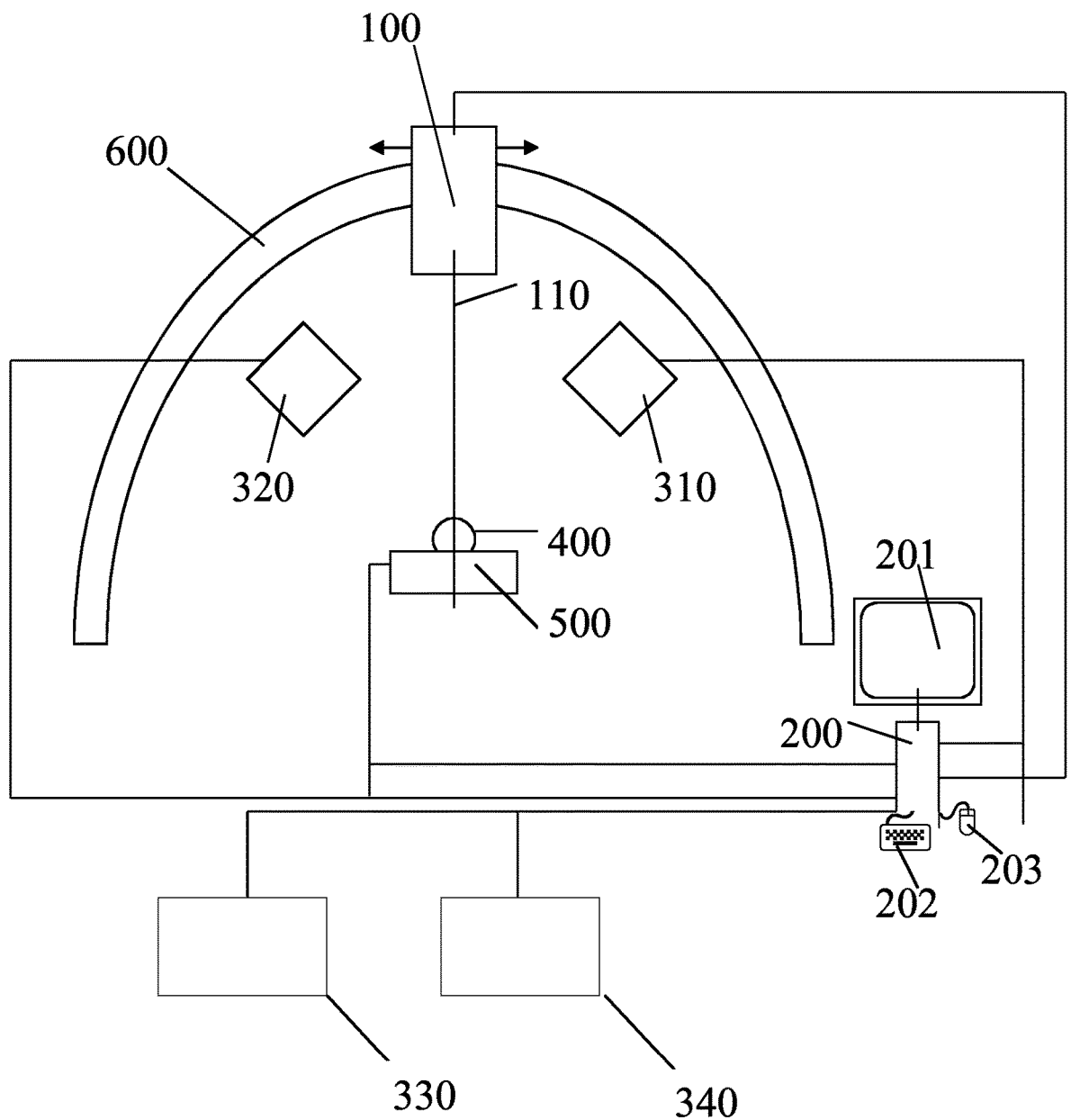
FIG. 9 shows a system according to at least one exemplary embodiment.

FIG. 9 shows at least one exemplary embodiment according to an aspect of the invention which is related to a system. The system comprises for example a computer 200. To the computer 200 is connected a monitor 201, a keyboard 202, and a mouse 203, for example. For example, the computer 200 is connected to the treatment device 100 which can, for example, be moved along an arc 600. For example, x-ray devices 310 and 320 are used to make a two-dimensional x-ray image from a patient 400 which is placed on a couch 500. Alternatively or additionally, the computer 200 can be connected to the couch 500 for changing the position of the couch 500. Alternatively or additionally, the computer 200 can be connected to an analytical device 330 for generating the 4D-CT. Additionally or alternatively, the computer 200 can be connected to the analytical device 340 for generating the planning CT. The connections described above are for example constituted to transfer image data. The connection can be wired or wireless.

Exemplary Steps of at Least One Example

According to an example, the different points in time assigned to respective sequence CTs referred to different breathing states of a patient. For example, the respective sequence CTs are assigned to 100% inhaled, 25% exhaled, 50% exhaled, 75% exhaled, 0% inhaled, 25% inhaled, 50% inhaled, 75% inhaled.

For example, one of the sequence CTs, to which a particular point in time (for instance particular respiratory state) is assigned, is selected as the undynamic CT. The selection is for instance performed as described in WO 2015/127970. That is, that one of the sequence CTs is selected as undynamic CT, in which the target is good discernible.

For example, in order to determine the primary and secondary trajectories, image fusion (for example elastic fusion) is performed for the different points in time (respiratory states).

For example, the undynamic CT acts as a source for the calculation of the trajectories. For example, elastic fusion mapping is used to get a first image element (target point) at a certain point in time (for instance certain phase of respiration) for every first image element of the undynamic image. For example, the image elements are voxels or cluster of voxels.

For example, the trajectory is defined by means of the image elements at different points in time. For example a trajectory is mathematically defined by T, then T={source point, target point (10%), target point (20%), . . . , target point (90%)}.

For example, the points of the trajectory describe positions of three-dimensional image elements for a particular point in time, for example of voxels or cluster of voxels. For example, the trajectory is a sorted list of the points. For example, the points are sorted by time (for example phase, for example phase of respiration).

Examples for calculating a measure of similarity for the trajectories is given in the following.

First example of calculation of a similarity measure is based on a sum of squared differences.

In the following, the abbreviation "SSD" stands for sum of squared differences. The abbreviations X, Y, Z stand for the coordinates of a three-dimensional coordination system within which the trajectory is described. The latter $T_1$ stands for example for a trajectory of a treatment body part, for example of an isocenter of the treatment body part or of center of mass of a treatment body part. That is $T_{1x}(i)$ is the x coordinate of the treatment body part at the time (for instance phase) "i". $\overline{T}_{1x}$ is the average x coordinate of the treatment body part averaged over all points in time (for example all states of respiration). Correspondingly, $T_{2x}$ stands for the x coordinate of an image element (for example voxel) of the undynamic CT at the point in time (i) and $\overline{T}_{2x}$ stands for the average x coordinate of this image element averaged over the different points in time (for example states of respiration). The calculation is for example as follows:

$$SSDX = \sum_{i=1}^{n} ((T_{1x}(i) - \overline{T}_{1x}) - (T_{2x}(i) - \overline{T}_{2x}))^2$$

$$SSDY = \sum_{i=1}^{n} ((T_{1y}(i) - \overline{T}_{1y}) - (T_{2y}(i) - \overline{T}_{2y}))^2$$

$$SSDZ = \sum_{i=1}^{n} ((T_{1z}(i) - \overline{T}_{1z}) - (T_{2z}(i) - \overline{T}_{2z}))^2$$

$$SSD_{XYZ} = \frac{w_x * SSDX + w_y * SSDY + w_z * SSDZ}{w_x + w_y + w_z}$$

The above equations represent an approach to compute a measure of similarity of trajectories based on sum of squared differences. $SSD_{XYZ}$ is an example for a trajectory similarity value or the result of applying a threshold function to $SSD_{XYZ}$ is an example for a trajectory similarity value.

According to another example, correlation and amplitude correspondence are determined separately for determining the measure of similarity. For example, as described below, the correlation and the amplitude correspondence can be mixed, after separate determination in order to determine a trajectory similarity value as a measure of similarity or can respectively be used as a measure of similarity.

According to an example, a normalized correlation coefficient is calculated as follows:

For all three dimensions x,y,z the correlation coefficient is computed separately and the average correlation coefficient is taken as final measure. One could also think about weighting the correlation coefficients e.g. if a tumor is moving with diaphragm I-S correlation coefficient y (I/S) should get more weight. The equations below describe computing the normalized correlation coefficient for x,y,z, and the combination to be taken as a trajectory similarity value. $T_1$ and $T_2$ have the meaning as described above, and n is the number of points of each trajectory.

$$CCX = \frac{\sum_{i=1}^{n}(T_{1x}(i) - \overline{T}_{1x})(T_{2x}(i) - \overline{T}_{2x})}{\sqrt{\sum_{i=1}^{n}(T_{1x}(i) - \overline{T}_{1x})^2 \sum_{i=1}^{n}(T_{2x}(i) - \overline{T}_{2x})^2}}$$

$$CCY = \frac{\sum_{i=1}^{n}(T_{1y}(i) - \overline{T}_{1y})(T_{2y}(i) - \overline{T}_{2y})}{\sqrt{\sum_{i=1}^{n}(T_{1y}(i) - \overline{T}_{1y})^2 \sum_{i=1}^{n}(T_{2y}(i) - \overline{T}_{2y})^2}}$$

$$CCZ = \frac{\sum_{i=1}^{n}(T_{1z}(i) - \overline{T}_{1z})(T_{2z}(i) - \overline{T}_{2z})}{\sqrt{\sum_{i=1}^{n}(T_{1z}(i) - \overline{T}_{1z})^2 \sum_{i=1}^{n}(T_{2z}(i) - \overline{T}_{2z})^2}}$$

$$CC_{XYZ} = \frac{w_x * CCX + w_y * CCY + w_z * CCZ}{w_x + w_y + w_z}$$

The above equations represent an example for an approached compute a similarity measure for describing the similarity between trajectories based on correlation coefficient. The abbreviation "CC" stands for correlation coefficient. $CC_{XYZ}$ is an example for a trajectory similarity value or the result of applying a threshold function to $CC_{XYZ}$ is an example for a trajectory similarity value.

To determine a trajectory similarity value, a correlation coefficient can be combined with a value which describes similarity of amplitude of trajectories. An exemplary approach is described below:

For correlation coefficients that exceed a certain threshold (e.g. 0.7) one could add a second threshold focusing on the amplitude. The more accordance in the absolute value of the value, the higher the value. Here an exemplary equation focusing on the main direction of the target, in this case inferior-superior (I-S), the breathing motion caused by the diaphragm.

$$A_{IS} = \frac{\text{Min}(A_1, A_2)}{\text{Max}(A_1, A_2)}$$

In the above equation $A_1$ describes the peak to peak amplitude of a trajectory of the treatment body parts (for example isocenter or center of mass of treatment body part). For example the amplitude is along a particular axis of the coordinate system or a long one of the axis described for instance by a rotational ellipsoidal. A2 describes the corresponding peak to peak amplitude of an image element of the undynamic CT. The terms "Min" and "Max" stand for the function of determining the minimum respectively the maximum of $A_1$ and $A_2$.

According to a further embodiment, the threshold value of the above described threshold function is changed in dependence on the similarity of amplitudes which is for example described by $A_{IS}$. $A_{IS}$ is an example for an amplitude similarity value.

As described above, the planning CT can be one of the sequence CTs (for example bins) of the 4D-CT or can be generated separately. In the following, examples for this are described.

A scenario is that the Planning CT is one of the bins of the 4DCT scan. Then, for example, the dynamic image is not registered to the treatment volume, that is the planning transformation is not performed. (Remark: A 4DCT scan consists of several volumes/bins, each volume/bin corresponding to a specific respiratory state. Typical labeling: 100% Inhaled, 25% Exhaled, 25% Exhaled, 75% Exhaled, 0% Inhaled, 25% Inhaled, 25% Inhaled, 75% Inhaled).

In case the Planning CT is not part of the 4DCT scan, the planning CT is registered to one of the sequence CTs (by using the planning transformation). The registration procedure and thus the determination of the planning transformation would mean for example a first rigid registration step (concentrating e.g. on bones) yielding a transformation that brings the two in a common coordinates system, followed by a second deformable registration yielding a second transformation which represents a deformation field. The combination of the first and second transformation represents an example for a planning transformation. The question which one of the sequence CTs to be used as undynamic CT:

If the planning CT was taken during a specific breathing phase one could register the planning CT to the sequence CT which corresponds to the same respiratory state.

One could also register consecutively to all sequence CTs, and select the most similar sequence CT as the undynamic CT. 'Most similar' could for instance mean selecting the registration that resulted in the fewest deformation around the target area.

Or as mentioned above, one could select that one of the sequence CTs in which the treatment body part is best discernable.

Or a combination of the above.

According to an example, the computer implemented method is constituted to display the dynamic DRRs in dependence on selected thresholds. In particular, the computer implemented method can be constituted that a user changes the threshold while getting immediate feedback of the effect of change of threshold by displaying the dynamic DRR. In more detail, this is for example as follows:

The computer implemented method can be constituted to display a page for defining the dynamic DRR. This page provides e.g. a slider enabling the user to set a certain threshold value used by the above described threshold function. A first page can show a very strict threshold resulting in a dynamic DRR nearly containing the treatment body part (target) only. Only voxels following exactly the same trajectory (normalized) are taken into account for rendering. In another page, the threshold can be decreased and thus more voxels—voxels whose trajectory is "very similar" to the target—are used for rendering the dynamic DRR.

The invention claimed is:

1. A computer implemented method for determining a two dimensional DRR referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, the computer implemented method comprising the following steps:

acquiring the 4D-CT;

acquiring a planning CT, the planning CT being a three dimensional image used for planning of a treatment of the patient, the planning CT being acquired based on at least one of the sequence CTs or independently from the 4D-CT;

acquiring a three dimensional image, referred to as undynamic CT, from the 4D-CT, the undynamic CT comprising at least one first image element representing the at least one primary anatomical element and second image elements representing the secondary anatomical elements;

acquiring at least one trajectory, referred to as primary trajectory, based on the 4D-CT, the at least one primary trajectory describing a path of the at least one first image element as a function of time;

acquiring trajectories of the second image elements, referred to as secondary trajectories, based on the 4D-CT;

for the image elements of the undynamic CT, determining trajectory similarity values based on the at least one primary trajectory and the secondary trajectories, the trajectory similarity values respectively describing a measure of similarity between a respective one of the secondary trajectories and the at least one primary trajectory;

determining the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

2. The computer implemented method according to claim 1, wherein image values of image elements of the dynamic DRR are determined in dependence on the trajectory similarity values used for determining the image elements.

3. The computer implemented method according to claim 1, wherein the undynamic CT is the planning CT; and
wherein the step of determining the dynamic DRR comprises at least one of the following steps:
determining the dynamic DRR by using the planning CT and the determined trajectory similarity values, wherein, during determination of the dynamic DRR from the planning CT, the trajectory similarity values are considered; or
determining another three dimensional image, referred to as dynamic planning CT by using the planning CT and by changing image values of the planning CT in dependence on the trajectory similarity values, and determining the dynamic DRR by digitally reconstructing the two-dimensional image from the dynamic planning CT.

4. The computer implemented method according to claim 1, wherein the step of acquiring the planning CT independently from the 4D-CT is performed and further comprising the steps of:
determining the planning transformation;
acquiring a three dimensional image referred to as similarity image from the determined trajectory similarity values related to the image elements of the undynamic CT;
applying the planning transformation to the similarity image;
wherein the step of determining the dynamic DRR comprises at least one of the following steps:

determining the dynamic DRR by using the planning CT and the determined trajectory similarity values, wherein, during determination of the dynamic DRR from the planning CT, image values of the transformed similarity image are considered; or
determining another three dimensional image, referred to as dynamic planning CT by changing image values of the planning CT in dependence on the corresponding trajectory similarity values of the transformed similarity image and determining the dynamic DRR by digitally reconstructing the two-dimensional image from the dynamic planning CT.

5. The computer implemented method according to one of claim 1, wherein the step of acquiring the planning CT independently from the 4D-CT is performed and further comprising the steps of:
determining the planning transformation; and
wherein the step of determining the dynamic DRR comprises:
determining a three dimensional image, referred to as dynamic CT by changing image values of at least a part of at least the second image elements of the undynamic CT in dependence on the trajectory similarity values determined for the respective image elements;
determining a three dimensional image referred to as dynamic planning CT by applying the planning transformation to the dynamic CT; and
determining the dynamic DRR by digitally reconstructing the two-dimensional image from the dynamic planning CT.

6. The computer implemented method according to claim 1 wherein the step of acquiring the primary and secondary trajectories comprises:
acquiring at least the at least one first image element from the undynamic CT;
acquiring the second image elements from the undynamic CT;
determining transformations referred to as sequence transformations which are constituted to transform the undynamic CT to one or more of the sequence CTs and/or to transform one of the sequence CTs to another one of the sequence CTs;
determining the trajectories of the at least one first image element and of at least some of the second image elements by applying the determined sequence transformation to the at least one first image element and the at least some of the second image elements.

7. The computer implemented method according to claim 1, further comprising a step of calculating trajectory similarity values as a measure of similarity between trajectories, the step comprising one of the following:
determining the respective trajectory similarity values as a function of positional differences between a first position of the at least one first image element defined by the at least one primary trajectory for different points in times and an average of the first position for the different points in time and a positional difference between a second position of a respective one of the second image elements defined by the secondary trajectory for the different times and an average of the second position for the different points in time, determining correlation coefficients describing a correlation between the trajectories;

determining a normalized correlation describing a normalized correlation between the trajectories;
determining amplitudes of the trajectories;
a combination of one of previous steps.

8. The computer implemented method according to claim 1 further comprising displaying of a superposition of the dynamic DDR over a two-dimensional X-ray image and/or aside the two-dimensional X-ray image.

9. A computer implemented method for determining a three dimensional image referred to as similarity image based on a 4D-CT and/or for determining a two-dimensional DRR referred to as dynamic DRR and/or for determining a three-dimensional image referred to as dynamic CT, the 4D-CT describing a sequence of three dimensional medical computer tomographic images of an anatomical body part of a patient which represent the anatomical body part at different points in time, the images being referred to as sequence CTs, the anatomical body part comprising at least one primary anatomical element and secondary anatomical elements, the computer implemented method comprising the following steps:
acquiring the 4D-CT;
acquiring a three dimensional image, referred to as undynamic CT, from the 4D-CT, the undynamic CT comprising at least one first image element representing the at least one primary anatomical element and second image elements representing the secondary anatomical elements;
acquiring at least one trajectory, referred to as primary trajectory, based on 4D-CT, the at least one primary trajectory describing a path of the at least one first image element as a function of time;
acquiring trajectories of the second image elements, referred to as secondary trajectories, based on the 4D-CT;
for the image elements of the undynamic CT, determining trajectory similarity values based on the primary trajectory and the secondary trajectories, the trajectory similarity values respectively describing a measure of similarity between a respective one of the secondary trajectories and the at least one primary trajectory; and
further comprising at least one of the following steps:
determining the similarity image by determining the trajectory similarity values to be image values of image elements of the similarity image, referred to as similarity image elements; and
optionally displaying the similarity image; or
determining the dynamic DRR by using the determined trajectory similarity values, at least a part of image values of image elements of the dynamic DRR being determined by using the trajectory similarity values; and optionally displaying the dynamic DRR; or
determining the dynamic CT by changing image values of at least a part of at least the second image elements of the undynamic CT in dependence on the trajectory similarity values determined for respective image elements and optionally displaying the dynamic CT.

10. The computer implemented method of claim 9, further comprising the step of acquiring a planning CT, the planning CT being a three dimensional image used for planning of a treatment of the patient, the planning CT being acquired based on at least one of the sequence CTs or independently from the 4D-CT; and
the positions of the similarity image elements correspond to the positions of the image elements of the undynamic CT to which the trajectory similarity values are respectively related;
and optionally, in case the planning CT is acquired independently from the 4D-CT, further determining a transformation from the undynamic CT to the planning CT and applying the transformation to the similarity image before displaying the similarity image.

11. A non-transitory computer-readable storage medium storing computer instructions executable by one or more processors to perform a method to determine a two dimensional DRR referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, the method comprising the following steps:
acquiring the 4D-CT;
acquiring a planning CT, the planning CT being a three dimensional image used for planning of a treatment of the patient, the planning CT being acquired based on at least one of the sequence CTs or independently from the 4D-CT;
acquiring a three dimensional image, referred to as undynamic CT, from the 4D-CT, the undynamic CT comprising at least one first image element representing the at least one primary anatomical element and second image elements representing the secondary anatomical elements;
acquiring at least one trajectory, referred to as primary trajectory, based on the 4D-CT, the at least one primary trajectory describing a path of the at least one first image element as a function of time;
acquiring trajectories of the second image elements, referred to as secondary trajectories, based on the 4D-CT;
for the image elements of the undynamic CT, determining trajectory similarity values based on the at least one primary trajectory and the secondary trajectories, the trajectory similarity values respectively describing a measure of similarity between a respective one of the secondary trajectories and the at least one primary trajectory;
determining the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

12. A system to determine a two dimensional DRR referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, comprising:
a computer having at least one processor to execute instructions stored on associated memory, the instructions when implemented, cause the at least one processor to:
acquire the 4D-CT;
acquire a planning CT, the planning CT being a three dimensional image used for planning of a treatment of the patient, the planning CT being acquired based on at least one of the sequence CTs or independently from the 4D-CT;

acquire a three dimensional image, referred to as undynamic CT, from the 4D-CT, the undynamic CT comprising at least one first image element representing the at least one primary anatomical element and second image elements representing the secondary anatomical elements;

acquire at least one trajectory, referred to as primary trajectory, based on the 4D-CT, the at least one primary trajectory describing a path of the at least one first image element as a function of time;

acquire trajectories of the second image elements, referred to as secondary trajectories, based on the 4D-CT;

for the image elements of the undynamic CT, determine trajectory similarity values based on the at least one primary trajectory and the secondary trajectories, the trajectory similarity values respectively describing a measure of similarity between a respective one of the secondary trajectories and the at least one primary trajectory;

determine the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

* * * * *